US00PP11923P2

(12) United States Plant Patent
Glicenstein

(10) Patent No.: US PP11,923 P2
(45) Date of Patent: Jun. 12, 2001

(54) AZALEA PLANT NAMED 'SPRING PROM'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/498,708

(22) Filed: Feb. 7, 2000

(51) Int. Cl.[7] ..... A01H 5/00

(52) U.S. Cl. ..... Plt./240

(58) Field of Search ..... Plt./238, 239, 240

(56) References Cited

U.S. PATENT DOCUMENTS

P.P. 6,607 * 2/1989 Motzkau ..... Plt./239

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Azalea plant named 'Spring Prom', characterized by its dark green leaves that do not abscise during the cooling and forcing periods; dense, uniform, mounded and outwardly spreading plant habit; freely branching habit; rapid flowering after forcing; numerous dark hot pink-colored flowers with ruffled petal margins; hose-in-hose flower form; excellent postproduction longevity with plants maintaining good flower substance for about four weeks in an interior environment; and very low incidence of infection with Cylindrocladium in inoculated trials.

2 Drawing Sheets

BACKGROUND OF THE INVENTION

The present Invention relates to a new and distinct cultiva of Azalea, botanically known as *Rhododendron hybrida*, an evergreen greenhouse-forcing type Azalea, and hereinafter referred to by the name 'Spring Prom'.

The new Azalea is a product of a planned breeding program conducted by the Inventor in Alva, Fla. The objective of the breeding program is to create new Azalea varieties having uniform plant habit and uniform flowering, numerous flowers, dark green foliage, good foliage retention during the cooling and forcing periods, resistance to Cylindrocladium, and excellent postproduction longevity.

The new Azalea originated from a cross made by the Inventor in Alva, Fla., of the commercial cultivar 'Prize', disclosed in U.S. Plant Pat. No. 3,795, as the male, or pollen, parent with the proprietary selection identified as code number YB-0160 as the female, or seed, parent.

Compared to plants of the male parent, the cultivar 'Prize', plants of the new Azalea have longer and narrower leaves; slightly smaller and brighter pink-colored flowers; differ in flower form; and are more resistant to Cylindrocladium in inoculation trials. Plants of the new Azalea differ from plants of the female parent, the proprietary selection identified as code number YB-0160, primarily in flower form and color.

The new Azalea was discovered and selected by the Inventor as a flowering plant within the progeny of the stated cross in a controlled environment in Alva, Fla., in June, 1993. The selection of this plant was based on its desirable flower color, profuse and uniform flowering, improved flower color retention, uniform plant habit, excellent postproduction longevity, and resistance to Cylindrocladium.

Asexual reproduction of the new Azalea by terminal cuttings taken in a controlled environment in Alva, Fla., has shown that the unique features of this new Azalea are stable and reproduced true to type in successive generations.

SUMMARY OF THE INVENTION

The new Azalea has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Spring Prom'. These characteristics in combination distinguish 'Spring Prom' as a new and distinct cultivar:

1. Dark green leaves that do not abscise during the cooling and forcing periods.
2. Dense, uniform, mounded and outwardly spreading plant habit.
3. Freely branching growth habit.
4. Rapid flowering after forcing.
5. Numerous dark hot pink-colored flowers with ruffled margins.
6. Hose-in-hose flower form.
7. Flowers that do not shatter.
8. Excellent postproduction longevity with plants maintaining good flower substance for about four weeks in an interior environment.
9. Very low incidence of infection with Cylindrocladium in inoculated trials.

Plants of the new Azalea can be compared to plants of the commercial cultivar 'YB 871 Remembrance', disclosed in U.S. Plant Pat. No. 9,132. In side-by-side comparisons conducted in Alva, Fla., plants of the new Azalea differ from plants of the cultivar 'YB 871 Remembrance' in the following characteristics:

1. Plants of the new Azalea are more vigorous and more upright than plants of the cultivar 'YB 871 Remembrance'.

2. Flower form of plants of the new Azalea is hose-in-hose, whereas flower form of plants of the cultivar 'YB 871 Remembrance' is single or semi-double.
3. Plants of the new Azalea last about 5 or 6 days longer in postproduction longevity trials than plants of the cultivar 'YB 871 Remembrance'.

BRIEF DESCRIPTION OF THE PHOTOGRAPHS

The accompanying colored photographs illustrate the overall appearance of the new Azalea. These photographs show the colors as true as it is reasonably possible to obtain in colored reproductions of this type. Colors in the photographs may differ slightly from the color values cited in the detailed botanical description, which accurately describe the actual colors of the new Azalea.

The photograph on the first sheet comprises a top perspective view of a typical plant of 'Spring Prom'.

The photograph at the top of the second sheet is a close-up view of typical flowers of 'Spring Prom'.

The photograph at the bottom of the second sheet comprises a close-up view of typical flowers of 'Spring Prom' (left) and 'YB 871 Remembrance' (right).

DETAILED BOTANICAL DESCRIPTION

The aforementioned and following observations, measurements, values, and comparisons describe plants grown in Alva, Fla., in 12.5-cm containers with day temperatures ranging from 16 to 35° C. and night temperatures ranging from 10 to 24° C. Plants were grown under 50 percent polypropylene shade cloth reducing ambient light levels to about 4,000 to 5,000 footcandles. Plants used for the description and photographs were about 12 months from planting. After flower bud development, plants were cooled at 3 to 5° C. for six weeks to break flower bud dormancy. Plants were subsequently forced into flower under commercial conditions in a polyethylene-covered greenhouse. In the following description, color references are made to The Royal Horticultural Society Color Chart except where general terms of ordinary dictionary significance are used.

Botanical classification:

*Botanical.*—*Rhododendron hybrida* 'Spring Prom'.

*Commercial.*—Evergreen greenhouse-forcing type Azalea.

Parentage:

*Male or pollen parent.*—*Rhododendron hybrida* cultivar 'Prize' disclosed in U.S. Plant Pat. No. 3,795.

*Female or seed parent.*—Proprietary *Rhododendron hybrida* selection identified as code number YB-0160.

Propagation:

*Type.*—By terminal cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Root description.*—Vigorous; finely-branched.

Plant description:

*Plant form and growth habit.*—Perennial, evergreen; mounded, outwardly spreading, inverted triangle; moderately vigorous. Freely flowering; numerous flowers per plant.

*Branching habit.*—Freely branching; about three or four lateral branches develop after removal of terminal apex.

*Plant height, soil level to top of flowers.*—About 27 cm.

*Plant diameter, area of spread.*—About 45 cm.

*Lateral branch description.*—Length: About 24 cm. Diameter at base: About 7 mm. Color: Immature: Between 144A and 144B. Mature: Woody, between 165A and 165B. Texture: Sparsely pubescent.

Foliage description:

*Arrangement.*—Alternate, single.

*Length.*—About 4.5 cm.

*Width.*—About 1.5 cm.

*Shape.*—Elongated elliptic to oblong.

*Apex.*—Mucronate.

*Base.*—Attenuate.

*Margin.*—Entire.

*Texture.*—Leathery; sparse pubescence on both surfaces.

*Color.*—Young foliage, upper surface: 147A. Young foliage, lower surface: 147B. Mature foliage, upper surface: Slightly darker than 147A. Mature foliage, lower surface: Close to 147B.

*Petiole.*—Length: About 7.5 mm. Diameter: About 1.5 mm. Color: 144A to 144B.

Flower description:

*Natural flowering season.*—Spring after sufficient cool period.

*Flower arrangement.*—Flowers arranged singly at terminals with usually about three flowers per apex. Flowers face upward and outward. Very freely flowering. Not fragrant.

*Flower appearance.*—Star-shaped hose-in-hose flower form with ruffled margins. Dark hot pink-colored petals. Flowers persistent.

*Flower diameter.*—About 6.5 cm.

*Flower depth.*—About 3.4 cm.

*Postproduction longevity.*—Inder interior conditions, plants maintain good flower substance for about four weeks.

*Flower bud* (*just starting to show petal color*).—Rate of opening: About three to four days depending on temperatures. Length: About 1.6 cm. Diameter: About 8 mm. Shape: Ovoid. Color: 57D.

*Petals.*—Arrangement: Hose-in-hose flower form; single whorl of five fused petals surrounded by whorl of sepals transformed into a complete whorl of petals. Length: About 4.4 cm. Width: About 2.75 cm. Shape: Roughly elliptic with rounded apex. Margin: Entire; undulating. Texture: Smooth, velvety. Color: When opening, upper surface: 57A to 57B. When opening, lower surface: 57B. Fully opened, upper surface: 57A to 57B; spots, close to 61B. Fully opened, lower surface: 57B to 57C. Throat: 57B to 57C.

*Sepals.*—Arrangement: Single whorl of five fused petal-like sepals. Length: About 3.7 cm. Width: About 2.6 cm. Shape: Roughly elliptic, but irregularly shaped with irregular apices and margins. Texture: Smooth, velvety. Color: Upper surface: 57A to 57B. Lower surface: 57B to 57C.

*Peduncles.*—Length: About 1.5 cm. Diameter: About 1.5 mm. Angle: Upright to bent with weight of flower. Strength: Flexible; strong. Texture: Very pubescent. Color: 144A.

*Reproductive organs.*—Androecium: Stamens: Typically about five. Anther shape: Oblong. Anther size: About 2 mm by 1 mm. Anther color: Close to 164B. Amount of pollen: Moderate. Pollen color: White, close to 155D. Gynoecium: Pistil number: One. Pistil length: About 3.3 cm. Stigma shape: Rounded. Stigma color: Close to 46A. Style length: About 2.7 mm. Style color: Close to 60B. Ovary color: 144A; heavily whiskered.

Disease resistance: Very low incidence of infection by Cylindrocladium in inoculated trials; trials repeated in Alva, Fla., during the summers of 1997, 1998 and 1999.

Seed production: Seed production has not been observed.

It is claimed:

1. A new and distinct Azalea plant named 'Spring Prom', as illustrated and described.

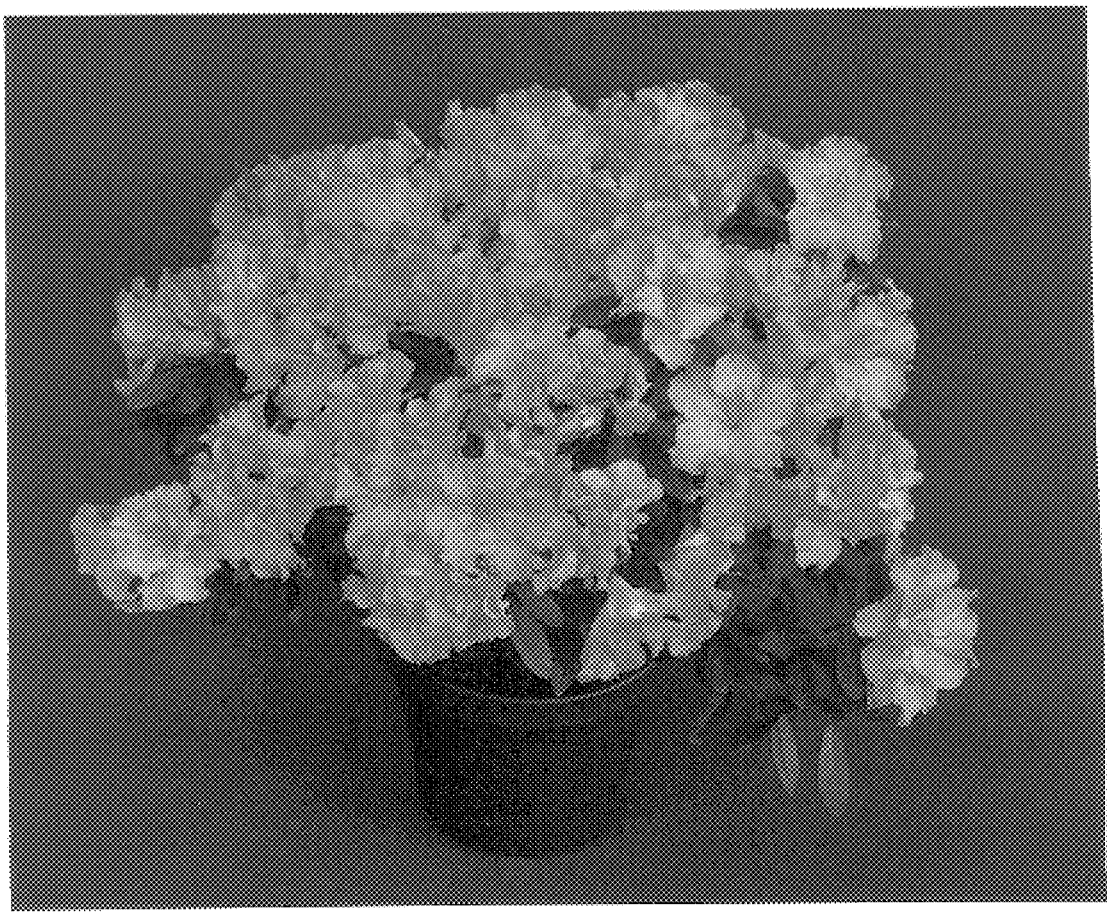

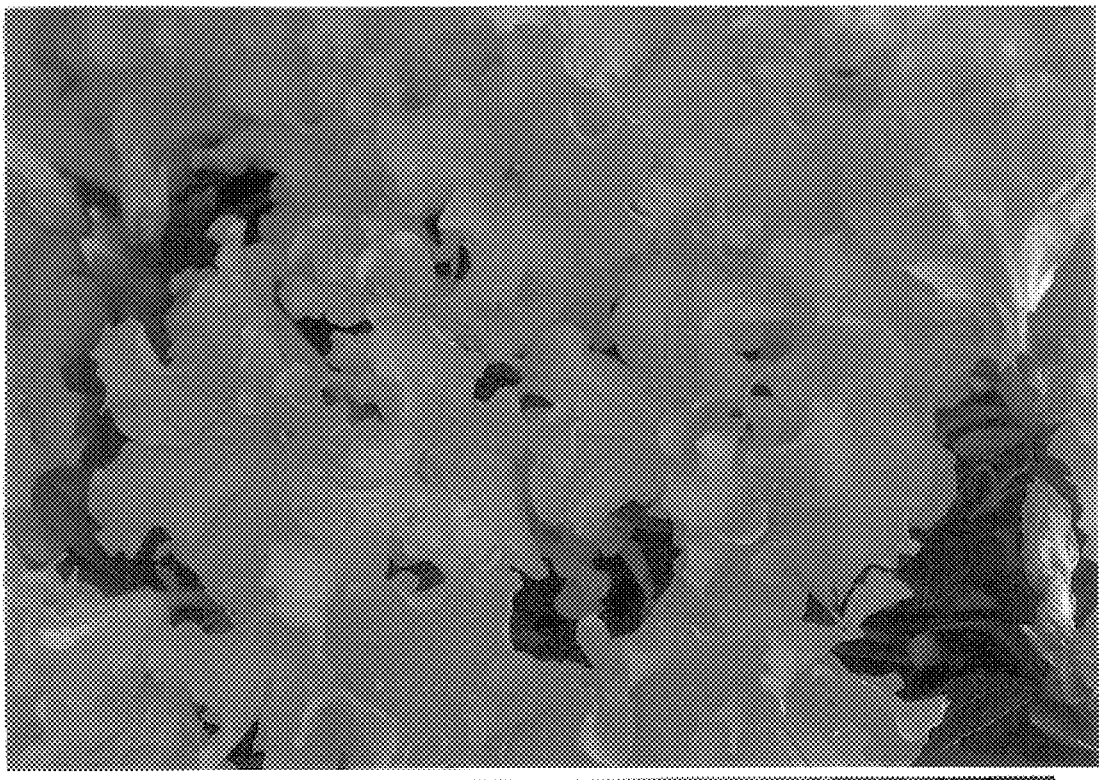
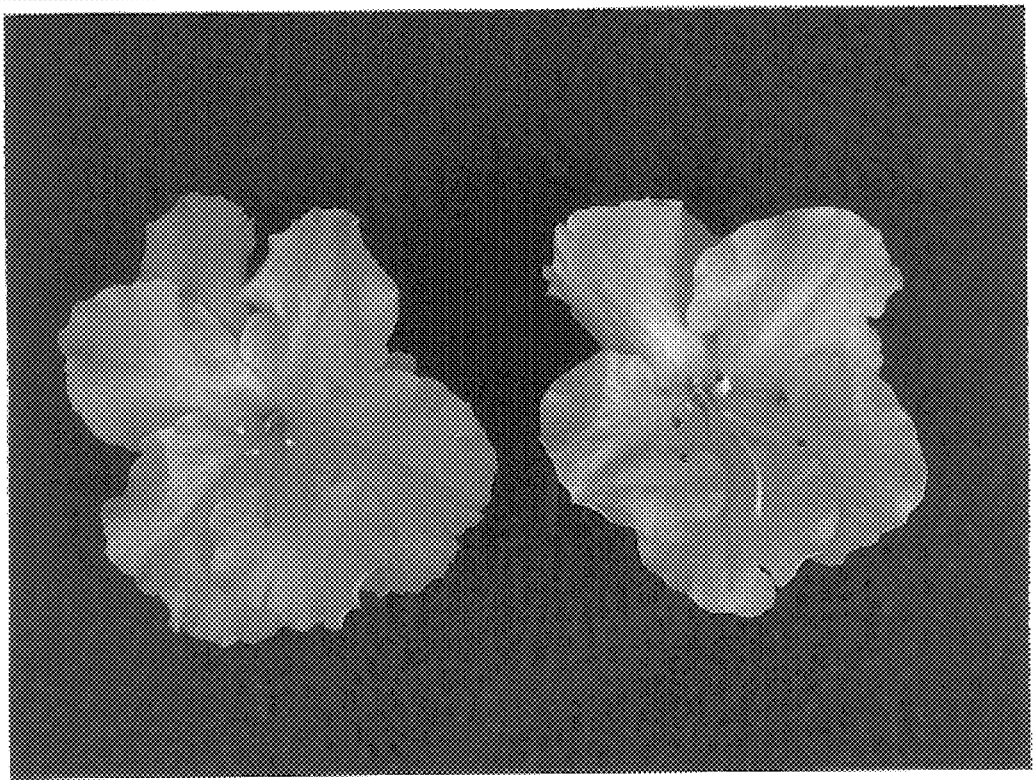

* * * * *